US008554505B2

(12) United States Patent
Vayhinger

(10) Patent No.: US 8,554,505 B2
(45) Date of Patent: Oct. 8, 2013

(54) SYSTEM AND METHOD FOR CALIBRATING AND MONITORING THE CONDITION OF A SENSOR DEVICE

(75) Inventor: Marcus Vayhinger, Schlieren (CH)

(73) Assignee: Mettler-Toledo AG, Greifensee (CH)

( * ) Notice: Subject to any disclaimer, the term of this patent is extended or adjusted under 35 U.S.C. 154(b) by 1146 days.

(21) Appl. No.: 12/119,874

(22) Filed: May 13, 2008

(65) Prior Publication Data
US 2009/0287445 A1 Nov. 19, 2009

(51) Int. Cl.
G01F 25/00 (2006.01)

(52) U.S. Cl.
USPC ............... 702/104; 73/1.06; 702/85; 702/100

(58) Field of Classification Search
USPC ............. 702/85, 99, 100, 104, 116, 130, 198; 73/1.06, 53.01, 597
See application file for complete search history.

(56) References Cited

U.S. PATENT DOCUMENTS

| 6,295,873 | B1 * | 10/2001 | Condreva | 73/597 |
| 6,685,807 | B2 | 2/2004 | Meier | |
| 6,856,930 | B2 | 2/2005 | Ammann | |
| 7,290,434 | B2 | 11/2007 | Ammann et al. | |
| 7,447,607 | B2 * | 11/2008 | Schuh et al. | 702/130 |
| 7,704,357 | B2 | 4/2010 | Pechstein | |
| 2006/0070889 | A1 | 4/2006 | Ehrismann | |
| 2006/0219575 | A1 | 10/2006 | Oberlin | |
| 2007/0214872 | A1 | 9/2007 | Ammann et al. | |
| 2008/0149497 | A1 | 6/2008 | Ehrismann | |

FOREIGN PATENT DOCUMENTS

| WO | 2007/006787 A1 | 1/2007 |
| WO | 2008/009676 A1 | 1/2008 |

OTHER PUBLICATIONS

Mettler-Toledo GMBH, "Low-maintenance pH electrodes and systems: Reduce your overall process costs!", Aug. 2001, 8 pages, Urdorf, Switzerland.
Mettler-Toledo GMBH, "InPro 2000 liquid-electrolyte pH electrodes with integrated temperature sensor.", Jan. 2002, 2 pages, Urdorf, Switzerland.
Mettler-Toledo GMBH, "InPro 3200(SG) gel-electrolyte pH electrodes with integrated temperature sensor.", Jan. 2002, 2 pages, Urdorf, Switzerland.
Mettler-Toledo GMBH, "Wartungsarme pH-Elektroden und pH-Systeme: So reduzieren Sie Ihre Prozesskosten.", Sep. 2002, 6 pages, Urdorf, Switzerland.
Mettler-Toledo GMBH, "InPro 2000 pH-Elektroden mit Fluessigelektrolyt und integriertem Temperaturfuehler.", Oct. 2000, 2 pages, Urdorf, Switzerland.
Mettler-Toledo GMBH, "InPro 3200(SG) pH-Elektroden mit Gelelektrolyt und integriertem Temperaturfuehler.", Jan. 2002, 2 pages, Urdorf, Switzerland.

(Continued)

*Primary Examiner* — John H Le
(74) *Attorney, Agent, or Firm* — Standley Law Group LLP

(57) ABSTRACT

A system and method allow a sensor device that is used in a process stream to be efficiently calibrated and monitored as to its operating condition. The sensor device is a measuring probe with a sensor portion, a memory device and an electrical input/output port, arranged so the memory device is in communication with both the sensor portion and the input/output port. The sensor device may be connected through an electrical connector to either a first external source, such as a personal computer having an input/output port, remote from the process stream, or a second external source, such as a transmitter, proximate to the process stream. Operating software is accessible to at least the first external source for monitoring and calibrating. Database software is accessible to each of the external sources, for storing data on every measuring probe used in the system.

2 Claims, 19 Drawing Sheets

(56) References Cited

OTHER PUBLICATIONS

Mettler-Toledo GMBH, "ISM Measuring systems "Intelligent Sensor Management"", Nov. 2005, 2 pages, Urdorf, Switzerland.
Mettler-Toledo AG, "Intelligent Digital pH and Oxygen Systems One Step Ahead of Maintenance", Jun. 2007, 4 pages, Urdorf, Switzerland.
Mettler-Toledo AG, "pH and DO Sensors with ISM® Technology", Aug. 2007, 8 pages, Urdorf, Switzerland.
Mettler-Toledo AG, "iSense Asset Suite Maximum Performance of ISM® Sensors", Dec. 2007, 2 pages, Urdorf, Switzerland.
Mortimer, C.E., "Das Basiswissen der Chemie", 1987, pp. 335-339, Georg Thieme Verlag, Stuttgart.

* cited by examiner

New Sensor Detected

A new sensor has been detected.

There is no information about this sensor stored in the database, yet. If you want to add the sensor to the database, please fill in the information below and click "Register Sensor".

Serial Number     XXXXXXX

Serial Model     InPro3253i/SG

TAG — 122

Description — 124

Comment — 126

Installation Area — 128

Register Sensor — 130

Cancel — 132

METTLER-TOLEDO iSense
iSense
ISM Asset Suite

142 TAG: XXXXXX    Sensor: InPro3253i/SG    Part No.: XXXXXXX    Serial No.: XXXXXXX    Communication Status Calibration Results (pH)

|  | Current Calibration |  | Last Adjustment (5/30/2007) |
|---|---|---|---|
| Slope | 58.10 mV (92%) | ☺ | 58.16 mV (100%) |
| Zero Point | 7.10 pH | ☺ | 7.03 pH |
| Response Time | 14 s | ☺ | 11 s |
| Glass Impedance | 325 MΩ | ☺ | 202 303 MΩ |
| Reference Impedance | 68 kΩ | ☺ | 58 kΩ |

Comment

Sensor Performance 106
Calibration 108
Sensor Database 110
Measurement 112

Adjust Sensor — 204    Save Calibration — 206    Reset Calibration — 208

210

Ready

METTLER-TOLEDO iSense iSense
ISM Asset Suite

142 TAG: XXXXXX  Sensor: InPro3253i/SG  Part No.: XXXXXXXX  Serial No.: XXXXXX  Communication Status

Measurement Data

Primary
4.01
pH

Secondary
77.0
°F

Tertiary
0
ORP/mV

242

Sensor Monitor pH-Input       178.0 mV
ORP-Input      0 mV
                  244
Temperature    25.0 °C
Glass Impedance 200 MΩ
Reference Impedance 60 kΩ

Actual Sensor Stress

246

Sensor Performance
106

Calibration
108

Sensor Database
110

Measurement
112

248

Ready

240

| iSense – Setup | | | | | |
|---|---|---|---|---|---|
| Data Backup | Database Maintenance | Buffer Management | Default Values | | |

Configured Buffers for pH Sensors

| Name | Buffertype ˅ | Standard Temperature Line |
|---|---|---|
| Mettler Toledo-9 | Standard | 2.00 4.01 7.00 9.21 |
| Mettler Toledo-10 | Standard | 2.00 4.01 7.00 10.01 |
| NIST Technical | Standard | 1.68 4.005 7.00 10.01 12.46 |
| NIST Standard (DIN 19266:2000-01) | Standard | 1.68 4.008 6.865 9.184 |
| Hach | Standard | 4.01 7.00 10.00 |

New Buffer

Remove

Selected pH Buffer Details

| Temperature | pH1 | pH2 | pH3 | pH4 | pH5 |
|---|---|---|---|---|---|
| 0.0 °C | 2.03 | 4.01 | 7.12 | 9.52 | |
| 5.0 °C | 2.02 | 4.01 | 7.09 | 9.45 | |
| 10.0 °C | 2.01 | 4.00 | 7.06 | 9.38 | |
| 15.0 °C | 2.00 | 4.00 | 7.04 | 9.32 | |
| 20.0 °C | 2.00 | 4.00 | 7.02 | 9.26 | |
| 25.0 °C | 2.00 | 4.01 | 7.00 | 9.21 | |
| 30.0 °C | 1.99 | 4.01 | 6.99 | 9.16 | |
| 35.0 °C | 1.99 | 4.02 | 6.98 | 9.11 | |
| 40.0 °C | 1.98 | 4.03 | 6.97 | 9.06 | |
| 45.0 °C | 1.98 | 4.04 | 6.97 | 9.03 | |
| 50.0 °C | 1.98 | 4.06 | 6.97 | 8.99 | |

Close

FIG-8C

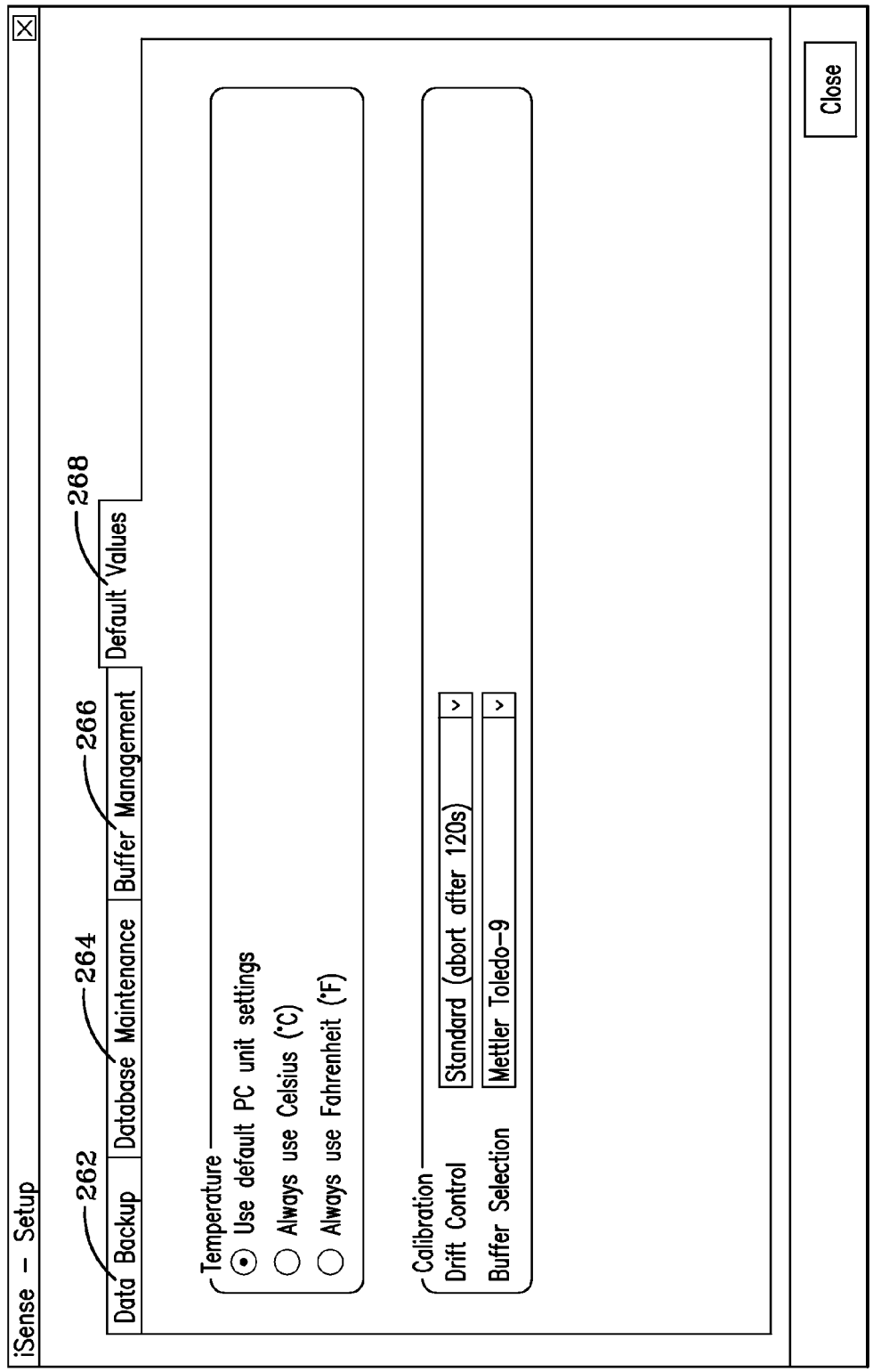

| iSense – Information | | | | | |
|---|---|---|---|---|---|
| Workstation | Language | Sensor Condition | System Information | License | Information |
| 282 | 284 | 286 | 288 | 290 | 292 |

Station Information

| | |
|---|---|
| Name | John Doe |
| Company | * Mettler Toledo |
| Department | * Business Development |
| Location | |
| Street, No. | * Im Hackacker 15 |
| City, State | * Urdorf |
| ZIP-Code | * 8907 |
| Country | * Switzerland |

* Mandatory fields for registration purposes.

Close — 294

| iSense – Information | | | | |
|---|---|---|---|---|
| Workstation | Language | Sensor Condition | System Information — 288 | License | Information |

System Information

| | |
|---|---|
| Logged-in User | X\ |
| Computer Name | XXXXXXXXXX |
| Date | Monday, March 17, 2008 |
| Time | 4:57:14 PM |
| Operating System | Microsoft Windows NT 5.1.2600 Service pack 2 |
| Registered To | Mettler-Toledo AG, Process Analytics, Bereich Informatik (76487-640-0325013-23354) |
| Physical Memory | 2048MB |
| Processor(s) | Intel(R) Core(TM)2 Duo CPU T7300 @2.00GHz, 1995MHz, 4MB L2-Cache, FSB 200M<br>Intel(R) Core(TM)2 Duo CPU T7300 @2.00GHz, 1995MHz, 4MB L2-Cache, FSB 200M |

[Close] — 294

FIG-9F iSense – Information

| Workstation | Language | Sensor Condition | System Information | License | Information |

Version
METTLER TOLEDO iSense
Version 1.0 02 Dev 1
Copyright METTLER TOLEDO AG
CH-8902 Urdorf, Switzerland License Agreement for METTLER TOLEDO iSense Software IMPORTANT– READ CAREFULLY: This License Agreement is a legal agreement between you ("Licensee") and Mettler-Toledo AG for the proprietary software product identified above, which includes computer software and may include associated media, printed materials, and "online" or electronic documentation ("SOFTWARE PRODUCT"). This SOFTWARE PRODUCT is made available to you only on the terms and conditions of this agreement. By installing, copying, or otherwise using the SOFTWARE PRODUCT (which ever occurs first), you agree to be bound by the terms of this agreement. If you do not agree with the terms of this agreement, you are not authorized to use the SOFTWARE PRODUCT. All rights not expressly granted to Licensee in this agreement are specifically reserved to Mettler-Toledo AG.

Software Product License

The SOFTWARE PRODUCT is protected by copyright laws and international copyright treaties, as well as other intellectual property laws and treaties. The SOFTWARE PRODUCT is licensed, not sold.

1. Grant of License.
Installation and Use. This agreement grants to you the non-exclusive and iSense
ISM Asset Suite

SYSTEM AND METHOD FOR CALIBRATING AND MONITORING THE CONDITION OF A SENSOR DEVICE

CROSS-REFERENCE TO RELATED APPLICATIONS

This application makes no claim of priority.

TECHNICAL FIELD

The disclosure relates to a system and method for monitoring and/or determining the condition of a sensor device, particularly, an analytical sensor, such as a pH electrode or a dissolved oxygen ("DO") sensor.

BACKGROUND OF THE ART

The control of many industrial processes is based upon the ability to measure at least one operating parameter using a probe or sensor that is immersed in a process fluid, especially a liquid.

In industry today, it is important to track the performance of production operations, especially when government regulatory authorities, such as the Food & Drug Administration ("FDA"), are implicated.

It is well documented that an important aspect of controlling and documenting production involves monitoring the operating condition of the very probes and instruments that monitor and control the production. This is particularly true with analytical probes, such as pH electrodes and DO sensors.

It is, therefore, an unmet objective of the prior art to provide a system and method that provides an individual electronic identity to each electrochemical sensor in use in the process, maintains an up to date record of the performance of the sensor, provides a realistic assessment of whether or not the sensor is fit for further use and provides a comprehensive maintenance history of all such sensors used.

SUMMARY OF THE DISCLOSED EMBODIMENTS

This objective is attained by a system for calibrating and monitoring the operating condition of a sensor device that comprises a measuring probe, a first and a second external source, a means for electrically connecting, an operating software component, and a database software component. The measuring probe has a sensor portion, a memory device and an electrical input/output port. The memory device is in electrical communication with the sensor portion and the electrical input/output port. The first external source comprises a personal computer with an input/output. It is located remote from the process stream. The second external source comprises a transmitter that is located proximate to the process stream. The electrical connecting means connects the memory device through the electrical signal output to one of the external sources. The operating software component is accessible to at least the first external source, but the database software component is accessible to each of the external sources. To perform a calibration of the measuring probe, it can be connected by its input/output port to a corresponding input/output port of the personal computer.

Other advantages are achieved by the system, when the measuring probe further comprises an electrical temperature sensor, in electrical communication with the memory device.

Still other advantages are achieved when the memory device in the memory probe is adapted to store a unique identifier for the probe and at least the most recent set of calibration data, including the date thereof.

In some aspects of the system, the operating software component is installed directly on the first external source.

In some aspects of the system, the measuring probe measures pH, while in others it measures dissolved oxygen.

Some of the advantages of the system are achieved by a method for measuring a chemical operating parameter of a liquid process stream. Such a process comprises the steps of:

providing a measuring probe, first and second external sources, the electrical connection means and the one of the external sources through the respective input/output ports; and the database software and operating software components as described above;

calibrating the measuring probe, using the electrical connecting means to communicate the measuring probe memory device to the first external source;

installing the calibrated measuring probe such that the sensor portion thereof is in contact with the liquid process stream;

monitoring simultaneously the operating condition of the installed measuring probe and measuring the chemical operating condition of the liquid processing stream, using the electrical connecting means to communicate the measuring probe memory device to the second external source; and repeating the calibrating, installing and monitoring steps as needed.

In some of the embodiments, the method further comprises the step of storing data from at least the most recent calibrating step in the memory device.

In some embodiments, the calibrating step is a two point interpolation calibration using a first and a second calibration standard.

BRIEF DESCRIPTION OF THE DRAWINGS

The details of the system and the method will be better understood when reference is made to the accompanying drawings, wherein identical parts are identified with identical reference numbers and wherein:

FIGS. 1 through 9 depict a number of screen shots from a software program that implements an embodiment of the invention on a personal computer.

DETAILED DESCRIPTION OF A PREFERRED EMBODIMENT

Figure 1:
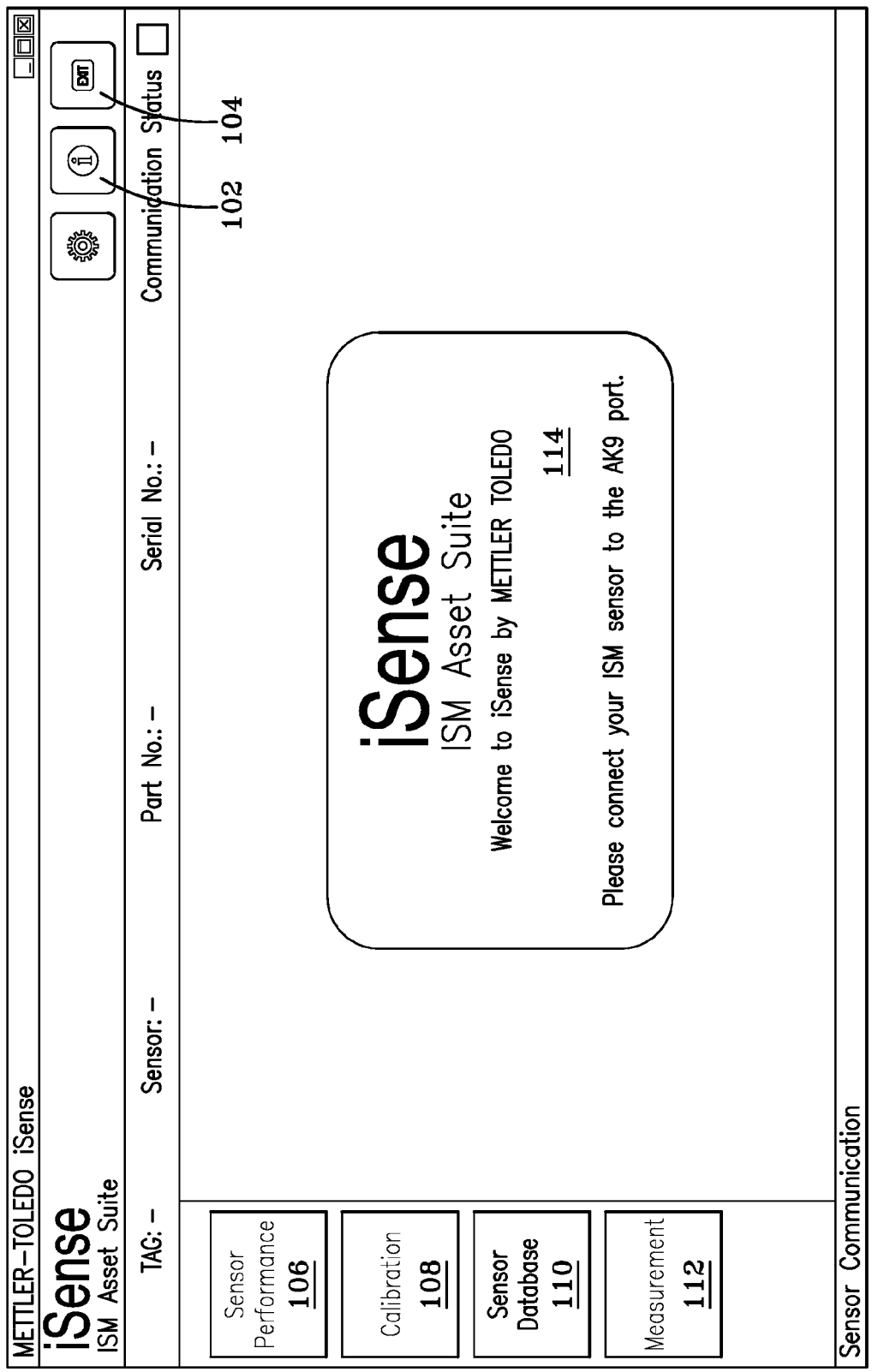

The system and method disclosed herein involve the interactive use of a measuring probe, a transmitter, and a computer unit that incorporates database software.

The Measuring Probe

A number of measuring probes are known in the art for measuring a parameter such as a particular ion concentration or redox potential of a liquid by measuring the electrical potential difference between two electrochemical half-cells.

One such measuring probe is disclosed in commonly-owned U.S. Pat. No. 6,685,807, to Meier, issued on 3 Feb. 2004, which is incorporated by reference as if fully recited herein.

Another such measuring probe is disclosed in commonly-owned U.S. Pat. No. 6,856,930, to Ammann, issued on 15 Feb. 2005, which is also incorporated by reference as if fully recited herein.

In some measuring probes of this type, the probe further has an electrical temperature sensor, such as a resistance temperature detector ("RTD"), incorporated into the probe. Description of a resistance temperature detector of this type is found in commonly-owned PCT application PCT/EP2007/057368, published 24 Jan. 2008 as WO 2008/009676, which is incorporated herein as if fully recited herein. When placed in the measuring probe, the RTD provides a voltage differential across the device that is monotonically related to the temperature.

In commonly-owned and co-pending U.S. patent application Ser. No. 11/704,941, which is incorporated by reference as if fully recited herein, a measuring probe, particularly a pH-measuring probe is disclosed. The pH probe has a sensor portion at which the voltage potential difference is measured. The pH probe also has a memory device incorporated into a body of the probe. Leads from the pH probe allow the electrical measurements to be conveyed directly to an external source, such as a transmitter. The electrical measurements can also be provided to the memory device where they may be stored. The memory device can also be connected to an external source, such as a personal computer, in which case an input/output port of the personal computer is used for the connection. While it is desirable to store as much "history" of a sensor as possible in the memory device, it will be understood that some data have a higher storage priority than other data. For example, it is necessary only to maintain a few sets of calibration data in memory, but other data, such as dates of calibration, remaining lifetime value, etc., will preferably be retained intact across the effective life of the probe.

A method for monitoring the function of a sensor, particularly a sensor for ozone, oxygen, chlorine, or hydrogen, is described in commonly-owned and co-pending US published application 2006/0219575, to Oberlin, which is incorporated by reference as if fully recited herein. Further information on monitoring sensor function or aging is found in the Amman '930 patent and the Meier '807 patent, both cited above.

Implementations of the invention described herein may be made with a number of measuring probes that are commercially available from Mettler-Toledo, including pH Models InPro325Xi, InPro4260i and InPro4800i and dissolved oxygen Models InPro6850i and InPro6900i. These probes are available in various electrode lengths.

The Personal Computer

Implementations of the invention described herein may be made with a variety of personal computers that are commercially available and that will be readily known to one of ordinary skill. A primary requirement for the personal computer is that it has an operating system that is compatible with the implementing software. As indicated in FIG. 11, the implementing software is operative on a personal computer with the Microsoft WINDOWS XP (or higher) operating system. Of course, it will be readily recognized that the implementing software should be readily able to be adapted to function appropriately on a variety of computer operating systems, and one skilled in such operating systems will be able to make the adaptations. For example, implementations of the software onto platforms such as UNIX or those provided by Apple Computer would be within scope of the invention as understood by the inventor.

It will further be recognized that the term "personal computer" is increasingly becoming a ubiquitous term to those of skill in this art, so implementations of the software onto devices such as personal data assistants ("PDAs"), etc., will be understood to be within the scope of the invention.

The Transmitter

A transmitter that is useful in exemplary embodiments of the invention may be purchased from Mettler-Toledo. A particularly useful embodiment is the Model M400 transmitter. The transmitter may have more than one measuring probe in electrical communication with it. For example, a single transmitter may be in electrical communication with both a pH probe and a DO probe.

The Database Software Component

The database software component is best understood from the description below of the operation of the software.

The Operating Software Component

A measuring probe used in an exemplary method has a sensor portion, which will typically be a sensor that determines an electrical potential difference, so there will be at least two electrodes with leads provided, the leads adapted for connection to means for determining the voltage difference. These leads are connected to external ports on the probe, so that the voltage difference determination can occur, as it usually has occurred in the past, external to the probe body. With a memory device being available inside the probe body, it is also possible and desirable to determine the voltage difference inside the probe and to store a numerical value related to the voltage difference in the memory device. The memory device should also be provided with at least a single external port for communication to and from the memory device. For these reasons, the probe will have at least one input/output connection point and possibly more. These may be grouped in a single port or plug. One example of the port is the type known as an AK9 port.

Similarly, personal computers are typically provided with a number of input/output ports, each of which may provide multiple connection points. These I/O ports are most commonly of a standardized nature, one standard being the USB 2.0 connection (USB stands for Universal Serial Bus). Other standards are known and available, including standards accepted by IEEE. However, once a port or plug is provided on the probe and a port type is selected on the personal computer, a connecting cable is trivially designed to make the desired connection. While many transmitters used in the operation being monitored may not presently be provided with the same type of connection port as the personal computer, this is only a minor inconvenience that requires that a different connection cable be used for connection of the probe to the transmitter. In a preferred situation, the use of a standard port in the transmitter allows the memory device on the probe to be in operative connection with the database.

Once the connection is made, the operating software component can be activated to effect data exchange with the measuring probe. The operating software component may be either directly installed on the personal computer or accessible to the personal computer from another computer connected thereto. An opening screen shot 100 for such an operating software component is shown as FIG. 1, where a preferred form of the software component is entitled iSENSE and is available from Mettler-Toledo. The operating software component is also referred to herein as the "implementing software." The screen shot 100 of FIG. 1 appears to be in a program such as VISUAL BASIC and many features will therefore be readily understood, due to the wide use of the symbols. For example, the button 102 is identifiable as the way to obtain information, button 104 is used to exit the program, etc. At the left side of screen 100 are buttons that allow access to program subsections, such as button 106 ("Sensor Performance"), button 108 ("Calibration"), button 110 ("Sensor Database') and button 112 ("Measurement").

As indicated in the central information area 114, the presence of the sensor is not being detected ("Please connect your ISM sensor to the AK9 port"), so the user is requested to connect the sensor, as this is necessary to proceed further in the program. An "AK9" port is a port design that is used in association with measuring probes of the type described above.

After connection of the probe, the first step would typically be a "handshake" to identify the measuring probe, as illustrated in the screen shot 120 of FIG. 2. Here, the connected probe has identified itself to the program as possessing a serial number of "6220003" and being a model "InPro3253i/SG", which is a standard probe designation of Mettler-Toledo AG of Greifensee, Switzerland, and its various affiliated companies around the world. Screen shot 120 indicates that the detected sensor is a "new" sensor, that is, one which has not been previously connected to the computer, or, more accurately, not previously identified in the database software component that is utilized by the computer. Four data boxes 122, 124, 126 and 128 allow the user to enter optional information about the detected sensor. Buttons 130 and 132, at the bottom left of the screen shot 120, allow the user to either register the sensor or to cancel the process, respectively. Because the buttons that allow access to program subsections (buttons 106, 108, 110 and 112 of FIG. 1) are not applicable with a new sensor until it is registered, they are not shown in FIG. 2.

Figure 3A:
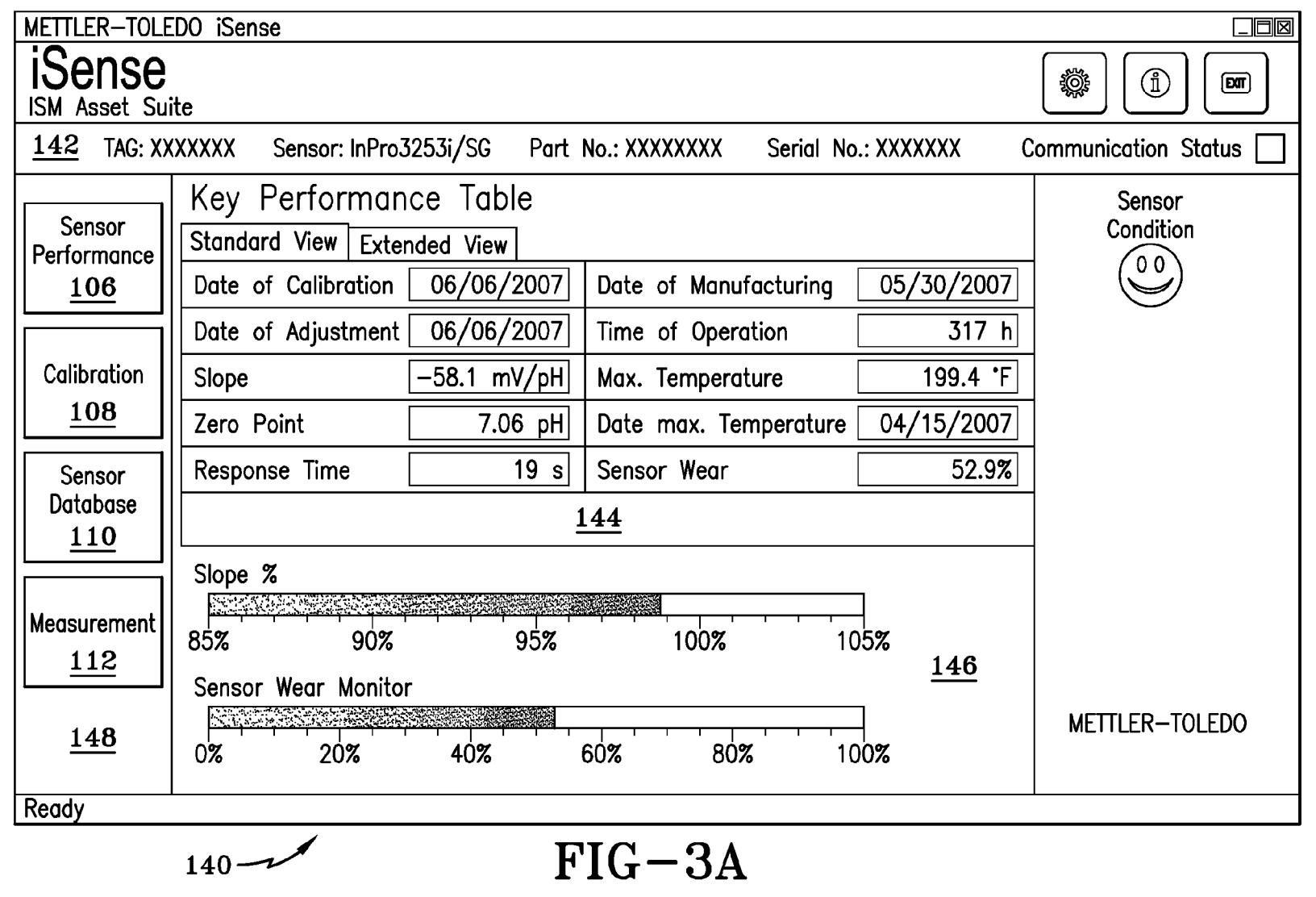
Figure 3B:

In contrast to FIG. 2, where a new sensor is detected, FIGS. 3A and 3B depict the screen shot 140 that is used when a sensor known to the database software component is identified or when the "Sensor Performance" button 106 is actuated. A box 142 across the upper portion of screen shot 140 provides not only the sensor serial number and model (both of which are internally stored in the sensor, as seen in FIG. 2), but also optional information that has been stored in the database software component about the sensor, such as the condition of the sensor. In one version of the "standard view", shown in central box 144 of FIG. 3A, the current information on the connected sensor are displayed, such as the dates of manufacture and calibration, as well as the date of adjustment. Other information about the sensor is available, such as the time of operation, slope, maximum temperature, zero point, date of maximum temperature, response time and sensor wear. The slope % and sensor wear monitor are presented graphically in a box 146 at the lower portion of the screen shot 140 of FIG. 3A. In the FIG. 3B variation, the quantitative value of sensor wear and the pictorial representation of sensor wear are replaced by the quantitative value of lifetime indicator (denominated in days) and the pictorial representation of the dynamic lifetime indicator. In both FIG. 3A and 3B, the overall sensor condition is represented pictorially at the upper right portion of the screen. A series of buttons in a box 148 at the left of the screen shot allow the user to move to the program subsections identified in FIG. 1, so these buttons 106, 108, 110 and 112, are identically identified as in FIG. 1. All of these data are stored in the probe memory. In a variation of this screen shot (not illustrated), an "extended view" representation of the "standard view" presented here may be shown.

Figure 4A:
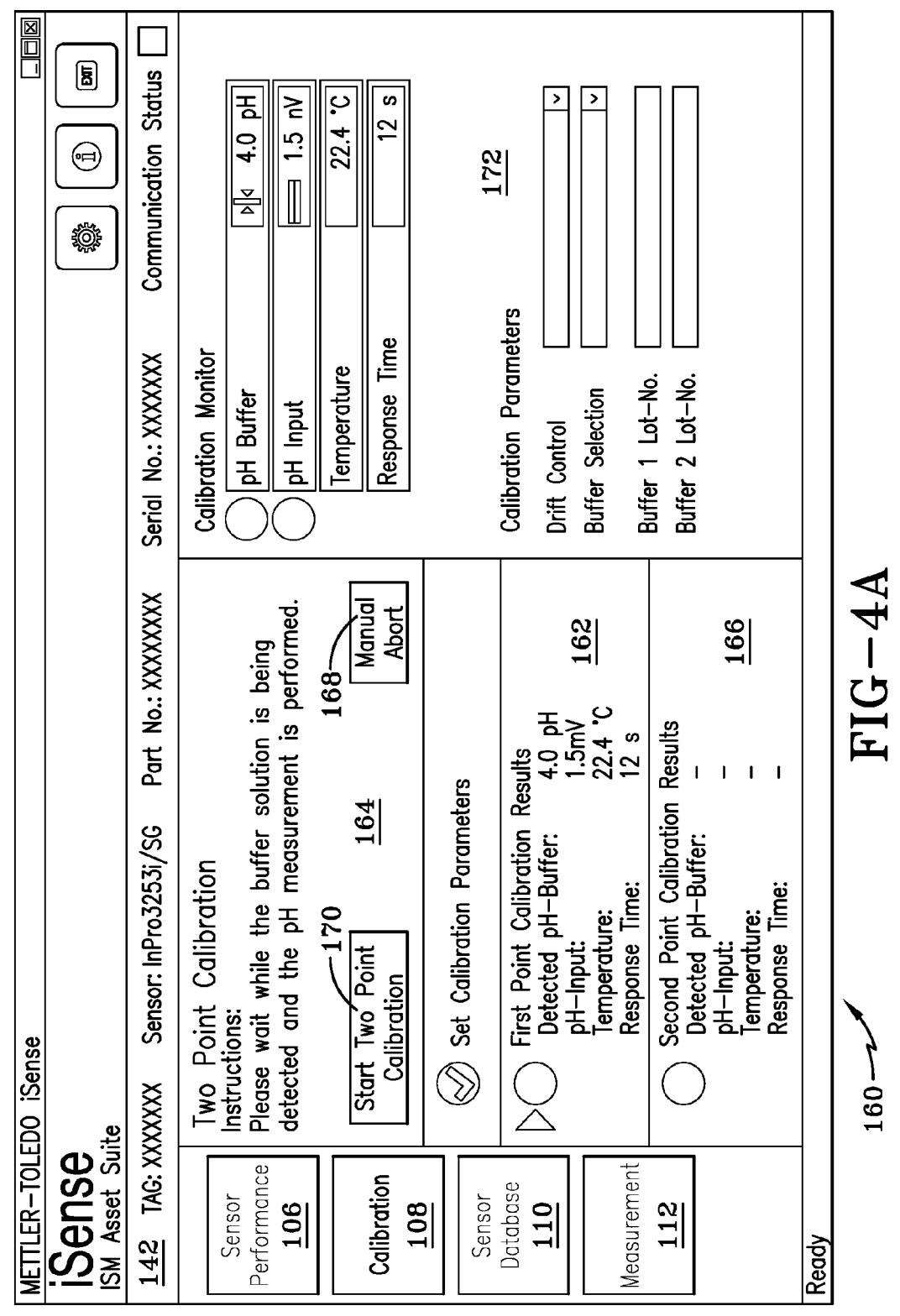

FIG. 4A shows a screen shot 160 that is reached through "Calibration" button 108, as depicted in several screen shots, including FIG. 1. The process depicted in screen shot 160 is a two-point calibration process conducted by immersing the probe sequentially in two standardized buffer solutions of known pH. As depicted, the calibration process is proceeding, with box 164 indicating that the first of the two calibrations has been conducted (at a pH of 4.0). The box 166 indicates that the second point of the calibration is proceeding. Because of this, the button 168, which would abort the calibration process, is available, but button 170, which would start the calibration, is not available. A box 172 at the lower right portion of the screen shot 160 allows entry of calibration parameters, such as entry of lot numbers of the buffers being used.

Figure 4B:
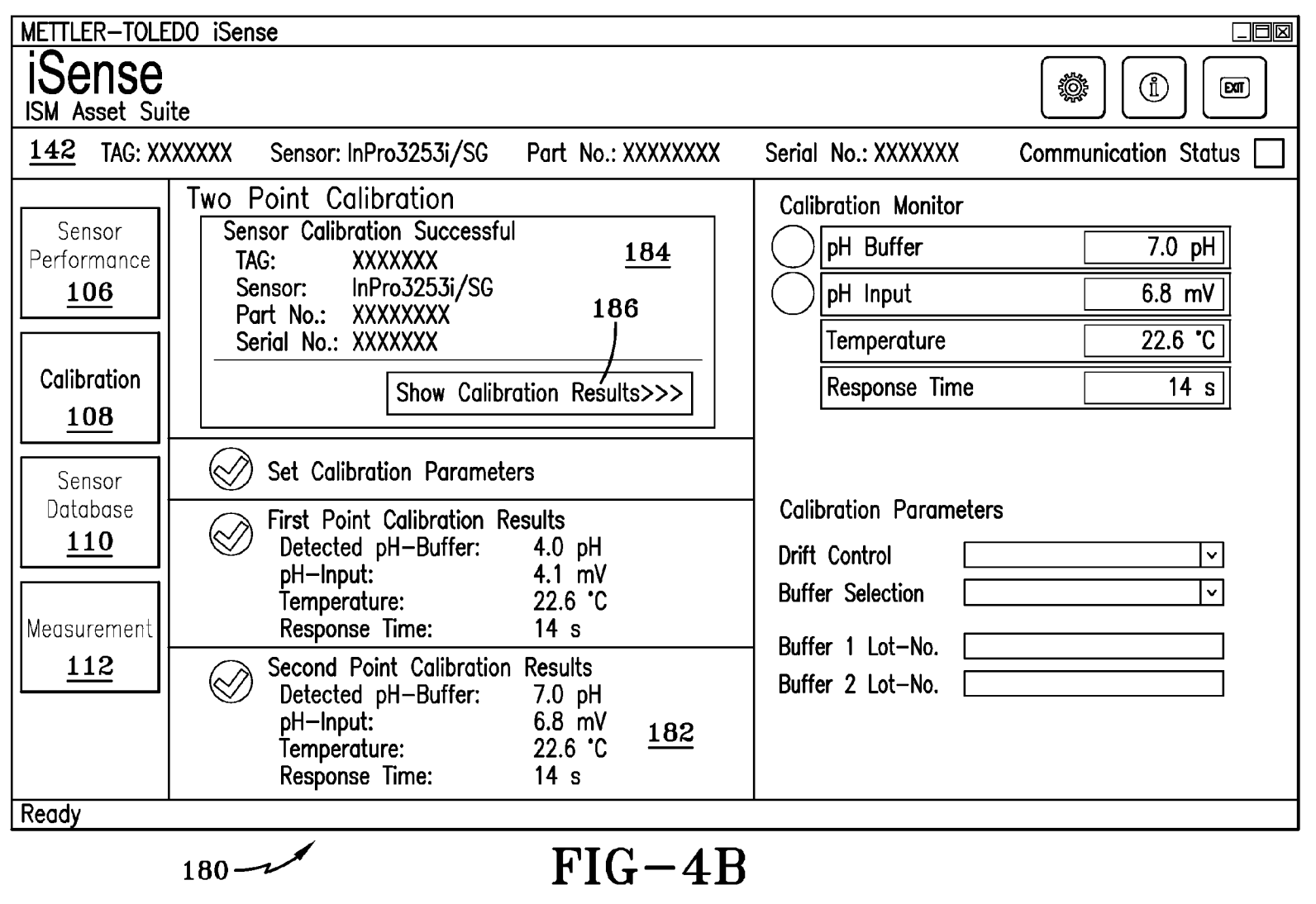

FIG. 4B shows a later depiction 180 of the screen shot shown in FIG. 4A. Screen shot 180 reports that the second point of the two-point calibration has been successfully completed. Many sections of the screen shot are identical to that of FIG. 4A, but a few sections have changed. For example, box 182 now shows that the second calibration was conducted at a pH of 7.0. Box 164 of FIG. 4A has been changed to the box 184 format of FIG. 4B, indicating that the calibration is complete. Box 184 also provides button 186, which allows the user to move to a screen showing calibration results for this sensor.

FIG. 5 depicts screen shot 200, which is a further part of the "Calibration" sequence and which is reached through button 186 of FIG. 4B. This screen shot 200 shows qualitative and quantitative results in central box 202, with qualitative results depicted with "emoticons". Options available to the user include three buttons at the lower portion of the screen, including button 204 ("Adjust Sensor"), 206 ("Save Calibration") and 208 ("Reset Calibration"). Box 210 at the left of the screen shot 200 provides standard buttons 106, 108, 110 and 112 as previously described. As in FIGS. 3 and 4, box 142 provides information on the sensor presently connected to the program. The calibration procedure is identical in algorithm and performance, whether performed through the program or through the M400 transmitter.

Figure 6:

FIG. 6 shows a screen shot 220 which reveals the subsection reached through button 110 ("Sensor Database"). While screen shot 220 shows only a single sensor (identified as "LIC1234"), the screen is designed to depict multiple sensors that are deployed. Upper and lower boxes 222, 224 allow the user to view summary information (in the upper box) on all of the sensors and, by selecting a particular sensor in the upper box, more detailed information can be viewed in the lower box. As before, box 142 identifies any sensor presently connected to the computer on which the operating software is being implemented.

The data in screen shot 220 are obtained not from the sensor itself, but from a database component, such as a SQL (Sequential Query Language) database. The database software component is distinct from the memory device onboard the measuring probe, although the data in the memory device should be consistent with that in the database software component. It is important to note that the calibration functionality of the personal computer and the software contained within it is not dependent upon a connection to the database, because the software can calibrate an attached measuring probe and download the calibration data to the memory device aboard the probe.

The term "deployed sensor" is intended to have a sufficiently broad meaning to encompass one or more individual probes of the appropriate type that are under control of a user, whether used in an industrial plant, an industrial plant with an accompanying quality control laboratory, or in a stand-alone laboratory. For example, the latter category may include a testing laboratory, exclusive of an industrial plant, but having a plurality of pH meters, could be within the scope of the term, provided that the transmitter units associated with the pH meters are adapted for electrical communication with the database component.

FIG. 7 shows a screen shot 240 that is reached through button 112 ("Measurement") and it depicts sensor detail information for sensors that are presently deployed. Such a sensor would be providing real-time data through a local transmitter that is communicated to the database. In the example shown, a first display area or box 242 provides quantitative data measured by the sensor, such as pH, temperature, and ORP/mV, this last parameter being recognizable as the oxidation reduction potential per mV. A second display area 244 shows sensor data, such as the voltages output by the device, the device temperature and device impedances. A third display area 246 depicts the level of sensor stress qualitatively. This screen shot 240 is not especially interactive, and the user navigates away from this screen using the buttons 106, 108, 110, 112 in display area 248, as previously discussed.

Figure 8A:
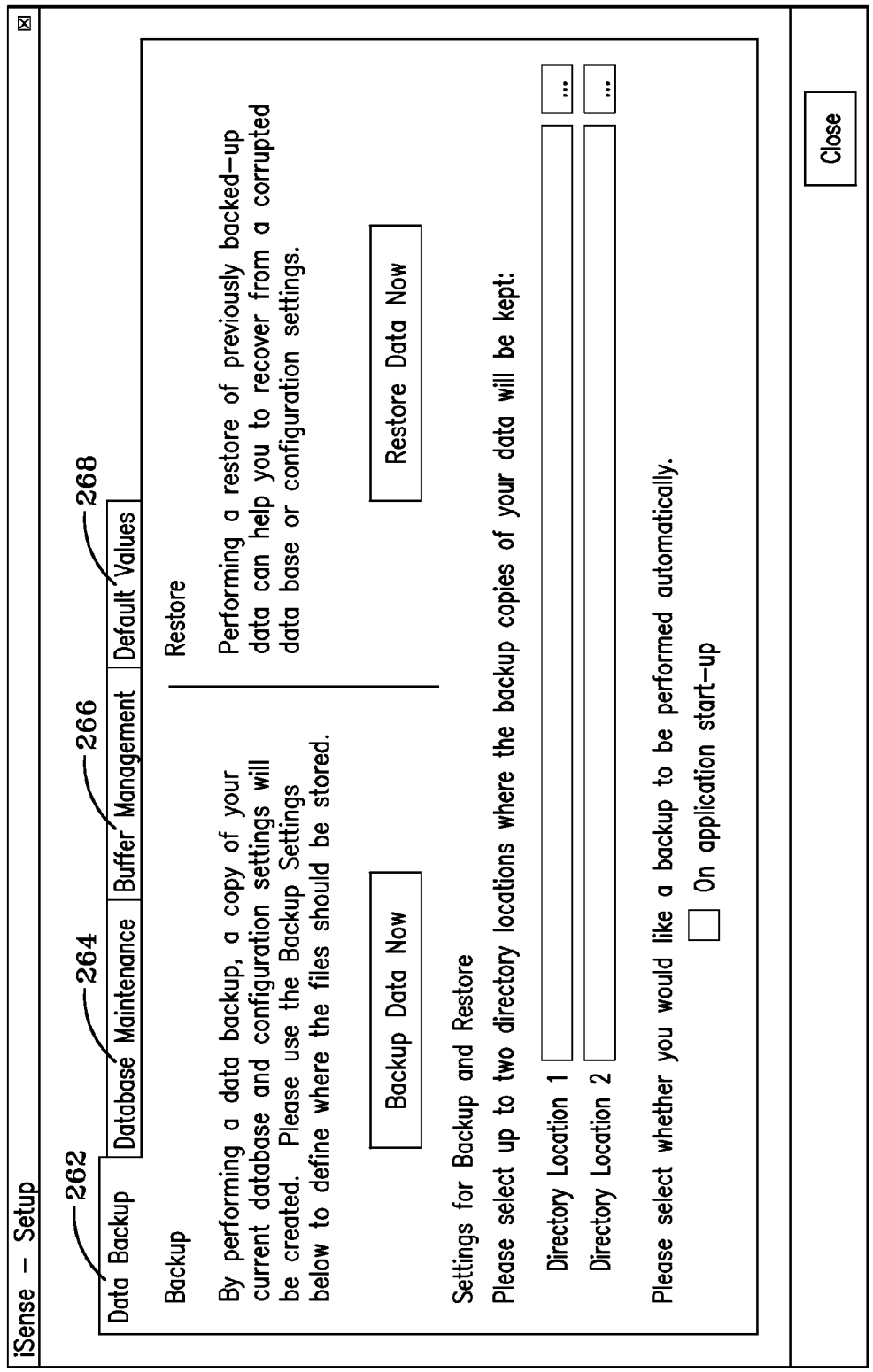
Figure 8B:
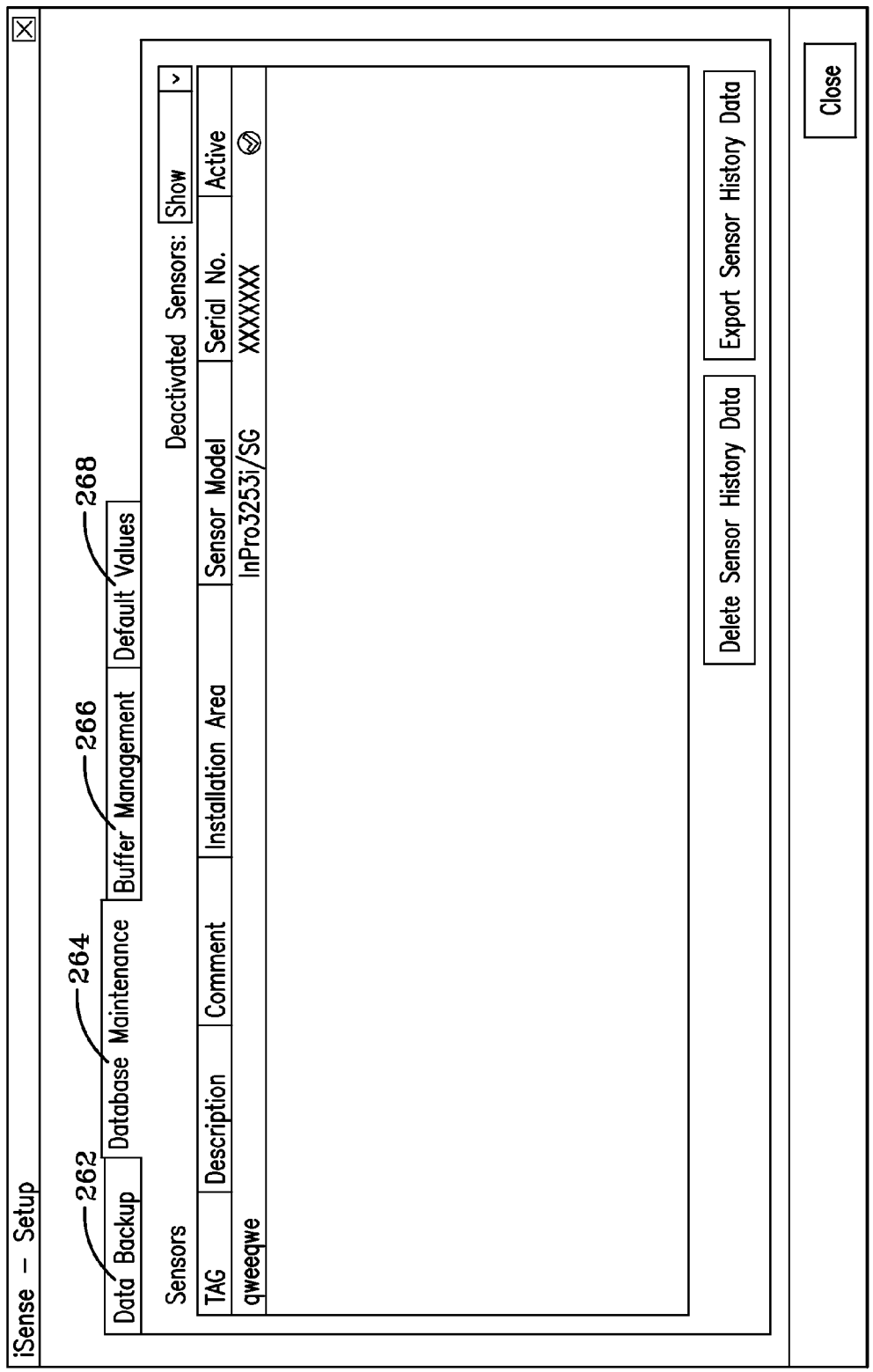

FIGS. 8A through 8D show a sequence of four "setup" screen shots 260 that are reached through the tabs 262, 264, 266 and 268. Details of the setup screen entitled "Backup" and reached through tab 262 is shown in FIG. 8A; details of the setup screen entitled "Database Maintenance" and reached through tab 264 is shown in FIG. 8B; details of the setup screen entitled "Buffer Management" and reached through tab 266 is shown in FIG. 8C; and details of the setup screen entitled "Default Values" and reached through tab 268 is shown in FIG. 8D.

Figure 9B:
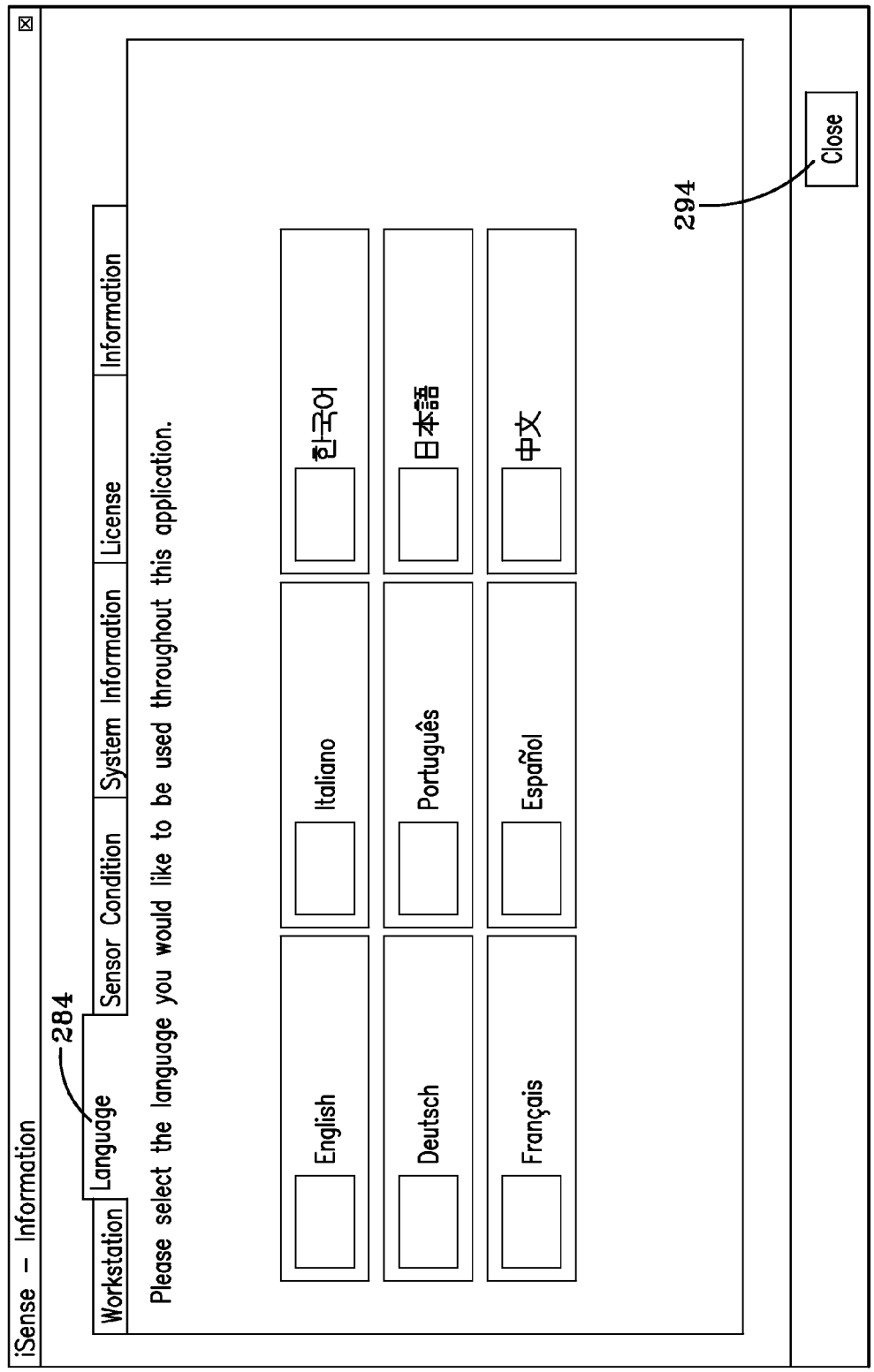
Figure 9C:
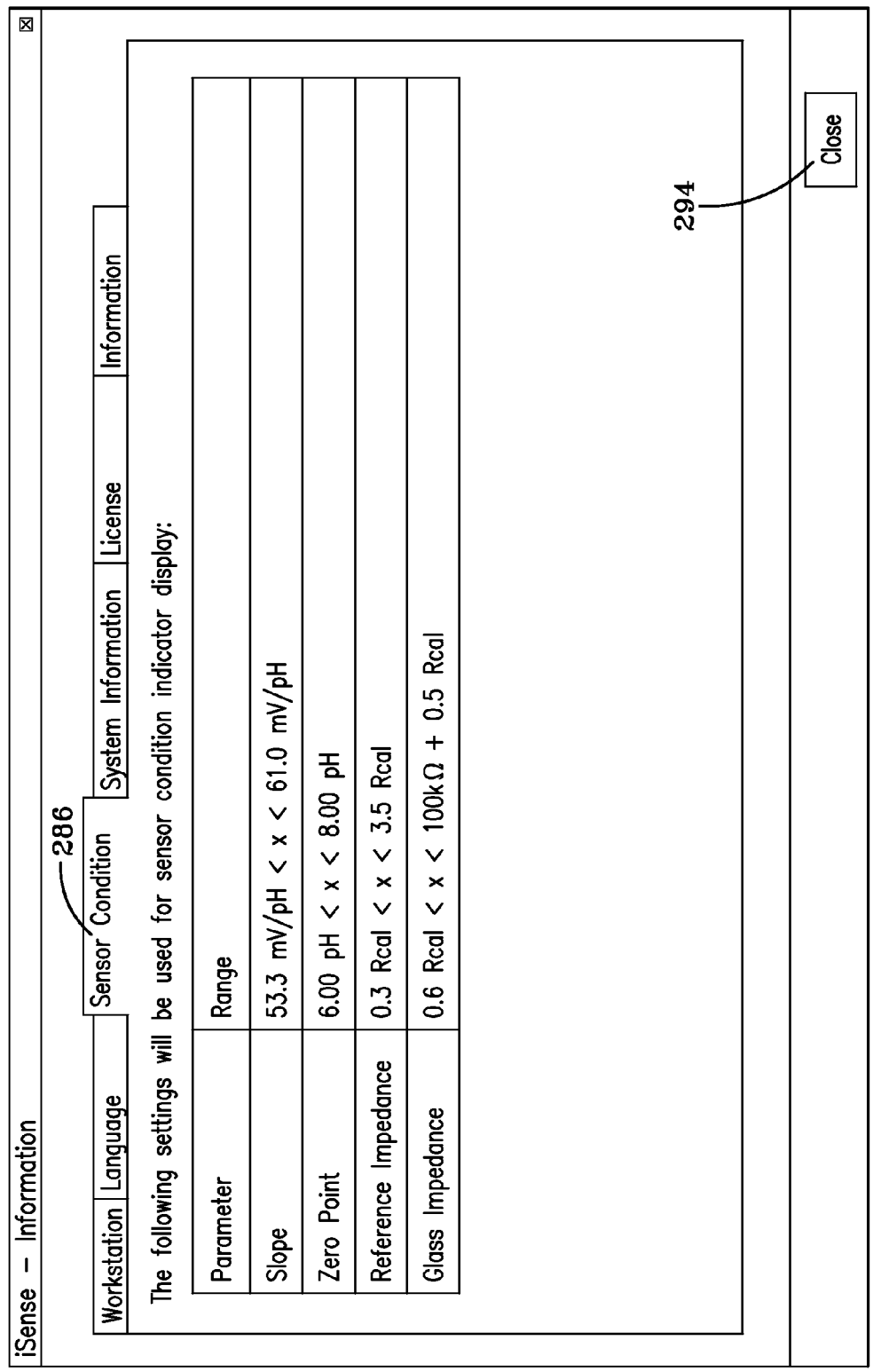
Figure 9E:
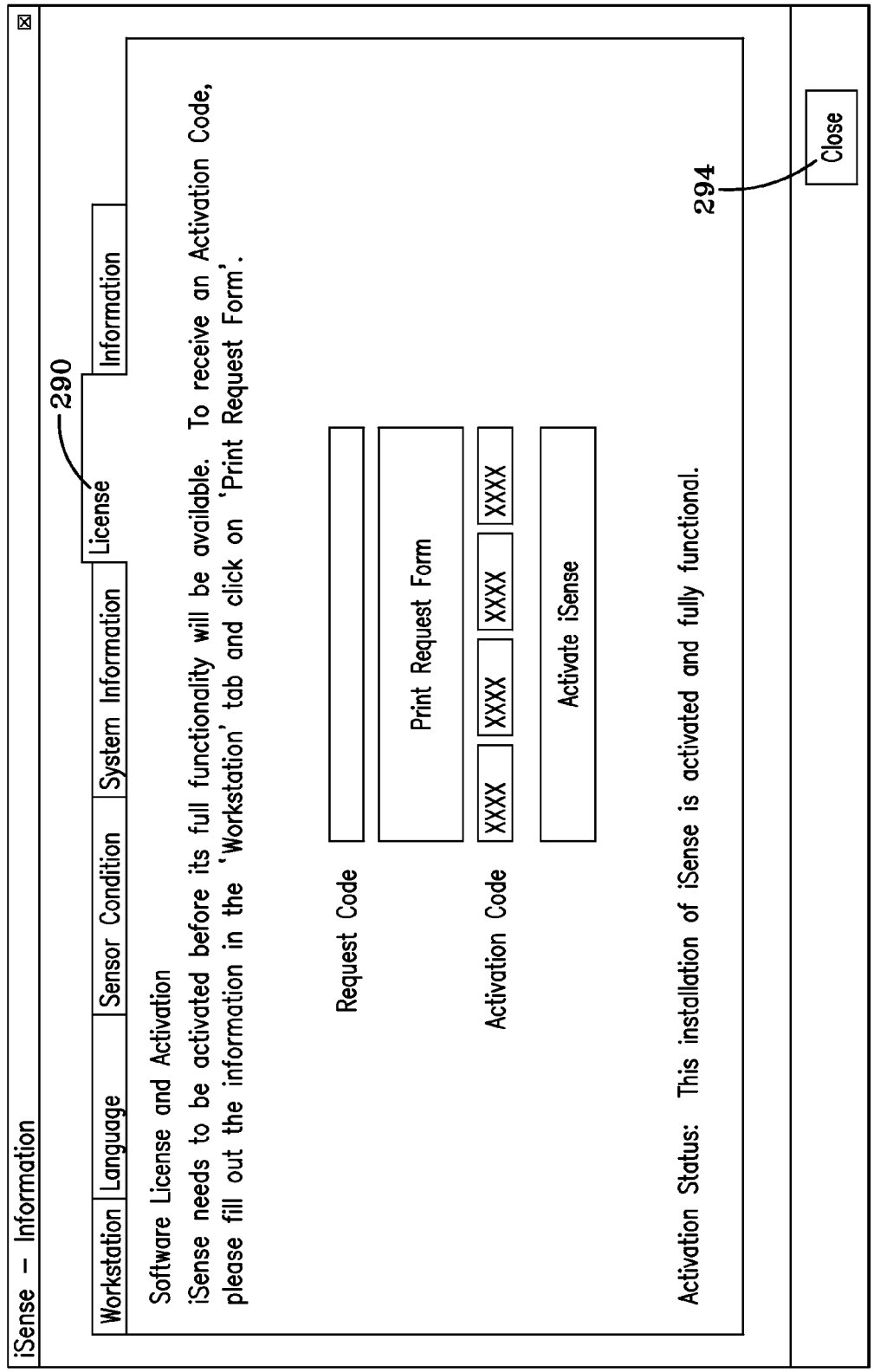

FIGS. 9A through 9F show a sequence of six "informational" screen shots 280. In the depiction of FIG. 9A, tabs 282, 284, 286, 288, 290 and 292 are shown, with the screen set on tab 282, which provides workstation information, such as user name, company, department, location and address. Many of these data are required for system registration. In the depiction of FIG. 9B, the screen 280 is set to tab 284, which allows the user to select the language to be used in the program, with nine options being provided. In the depiction of FIG. 9C, the screen 280 is set to tab 286, which allows the user to select the sensor condition parameters and ranges for display. In the depiction of FIG. 9D, the screen 280 is set to tab 288, which displays information on the computer on which the implementing software is deployed. In the depiction of FIG. 9E, the screen 280 is set to tab 290, which displays information on the license status and allows an activation code to be provided. In the depiction of FIG. 9F, the screen 280 is set to tab 292, which displays the terms and conditions of the software license. At each of the screen variations 290, a box 294 allows the user to exit the various information screens. These features are common to computer software of this type and will be readily understood as not critical to the specific embodiment taught herein. Typically access to the various information screen shots 290 will be obtained through information button 102 on any of screen shots 100, 140, 160, 180, 200, 220 or 240.

Monitoring Operation

As is seen in FIGS. 6 and 7, the database and implementing software may be in operative communication with the deployed probes that are connected through transmitters. As particularly shown in FIG. 7, the status of each probe that is connected to the database may be monitored through any computer units that have access to the database. This connection may be a "hard wire" or wireless connection or it may be a web-based connection.

Centralized Database and History Documentation

Although the above description discusses the exemplary database component without any discussion of other process control software, an important aspect of the database component is the ability to seamlessly implement the invention into production systems in a reliable manner. For that reason, it is a highly desirable object to integrate the database, and, indeed, the entire system discussed herein, into the existing process control system.

Maintenance Concepts

The database and implementing software as described herein provide the opportunity to deploy a new concept for maintaining the involved sensors.

In one example, the individual sensors may be pre-calibrated in a laboratory setting, under stable and controllable ambient conditions, rather than at the process line location where the sensor will be deployed. The more controlled calibration minimizes or, potentially, eliminates the risks associated with an inaccurate calibration.

In a further example, the pre-calibration of a sensor allows swift exchange at the process line. When a need for a sensor exchange is determined, dispatching a pre-calibrated sensor to the location permits a shorter process interruption (or a shorter loss of real-time process monitoring). There is no need to evaluate the replaced sensor at the process line location, as it may be returned to the laboratory for evaluation under the more controlled conditions.

Beyond the advantages described above, the system reduces the consequences associated with unexpected process interruptions, including, for exemplary purposes only, added costs, environmental risks and safety hazards, through early detection of measuring probes that are nearing their end-of-life or are in critical status.

What is claimed is:

1. A method for measuring a chemical operating parameter of a liquid process stream, comprising the steps of:
   providing:
      a measuring probe with a sensor portion, a memory device in electrical communication with the sensor portion and an input/output portion that is in electrical communication with at least one of the sensor portion and the memory device, the sensor portion adapted for measuring the chemical operating parameter;
      a first external source, comprising a personal computer, remote from the process stream, with an input/output port;
      a second external source, comprising a transmitter, proximate to the process stream, with an input/ouput port;
      a means for electrically communicating the measuring probe to one of the external sources through the respective input/output ports;
      an operating software component, accessible to the first external source; and
      a database software component, accessible to each external source;
   calibrating the measuring probe, using the electrical communicating means to communicate the measuring probe memory device directly to the first external source, where the calibrating step is a two point interpolation calibration using a first and a second calibration standard;
   installing the calibrated measuring probe such that the sensor portion thereof is in contact with the liquid process stream;
   monitoring simultaneously the operating condition of the installed measuring probe and measuring the chemical operating condition of the liquid processing stream, using the electrical communicating means to communicate the measuring probe memory device to the second external source; and repeating the calibrating, installing and monitoring steps as needed.

2. The method of claim 1, further comprising the step of:

storing data from at least the most recent calibrating step in the memory device.

* * * * *